US009797896B2

United States Patent
Ding (10) Patent No.: US 9,797,896 B2
(45) Date of Patent: Oct. 24, 2017

(54) REAGENT ZONE DEPOSITION PATTERN (71) Applicant: Ortho-Clinical Diagnostics, Inc., Raritan, NJ (US)

(72) Inventor: Zhong Ding, Pittsford, NY (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 51 days.

(21) Appl. No.: 14/178,327

(22) Filed: Feb. 12, 2014

(65) Prior Publication Data

US 2014/0227721 A1    Aug. 14, 2014

Related U.S. Application Data (60) Provisional application No. 61/763,662, filed on Feb. 12, 2013.

(51) Int. Cl.
*G01N 33/543* (2006.01)
*B01L 3/00* (2006.01)
*G01N 33/558* (2006.01)

(52) U.S. Cl.
CPC ...... *G01N 33/54393* (2013.01); *B01L 3/5023* (2013.01); *B01L 3/502746* (2013.01);
(Continued)

(58) Field of Classification Search
CPC ........... G01N 33/54393; G01N 33/558; G01N 33/54386; B01L 3/5023; B01L 3/502746;
(Continued)

(56) References Cited

U.S. PATENT DOCUMENTS 5,120,643 A    6/1992  Ching et al.
5,559,041 A    9/1996  Kang et al.
(Continued)

FOREIGN PATENT DOCUMENTS

CN    101506657 A    8/2009
CN    101528350 A    9/2009
(Continued)

OTHER PUBLICATIONS

European Search Report for EP 14154484.1; dated Aug. 8, 2014; 2 pages.
(Continued)

*Primary Examiner* — Rebecca Martinez
(74) *Attorney, Agent, or Firm* — Barclay Damon, LLP (57) ABSTRACT

An assay device includes: a liquid sample zone; a reagent zone downstream and in fluid communication with the sample zone that includes a reagent cell having a line of symmetry in the direction of fluid flow; a reagent material in the reagent cell, wherein the reagent material includes a first reagent material located at the axis of symmetry and is left-right symmetric, and a second and third reagent material having a substantially identical shape and volume and located in mirror locations from the line of symmetry; a detection zone in fluid communication with the reagent zone; and a wicking zone in fluid communication with the detection zone having a capacity to receive liquid sample flowing from the detection zone. The sample addition zone, the detection zone and the wicking zone define a fluid flow path.

14 Claims, 8 Drawing Sheets

(52) U.S. Cl.
CPC ..... *G01N 33/54386* (2013.01); *G01N 33/558* (2013.01); *B01L 2200/0621* (2013.01); *B01L 2200/0636* (2013.01); *B01L 2200/16* (2013.01); *B01L 2300/0816* (2013.01); *B01L 2400/0406* (2013.01); *B01L 2400/086* (2013.01)

(58) Field of Classification Search
CPC ..... B01L 2200/0621; B01L 2200/0636; B01L 2200/16; B01L 2300/0816; B01L 2400/0406; B01L 2400/086
See application file for complete search history.

(56) References Cited

U.S. PATENT DOCUMENTS

| | | | |
|---|---|---|---|
| 5,714,389 | A | 2/1998 | Carlton et al. |
| 6,139,800 | A | 10/2000 | Chandler |
| 6,228,660 | B1 | 5/2001 | May et al. |
| 6,271,040 | B1 | 8/2001 | Buechler |
| 6,372,542 | B1 | 4/2002 | Martin et al. |
| 6,733,682 | B1 | 5/2004 | Björkman et al. |
| 6,811,736 | B1 | 11/2004 | Ohman et al. |
| 6,884,370 | B2 | 4/2005 | Ohman et al. |
| 7,416,700 | B2 | 8/2008 | Buechler et al. |
| 8,409,523 | B2 | 4/2013 | Mendel-Hartvig et al. |
| 2002/0160525 | A1 | 10/2002 | Kang et al. |
| 2003/0124623 | A1 | 7/2003 | Yager et al. |
| 2005/0042766 | A1 | 2/2005 | Ohman et al. |
| 2006/0239859 | A1 | 10/2006 | Ohman et al. |
| 2006/0285996 | A1 | 12/2006 | Ohman et al. |
| 2006/0289787 | A1 | 12/2006 | Ohman et al. |
| 2007/0231883 | A1 | 10/2007 | Lindstrom et al. |
| 2009/0311805 | A1 | 12/2009 | Bergman et al. |

FOREIGN PATENT DOCUMENTS

| | | |
|---|---|---|
| CN | 101957354 A | 1/2011 |
| EP | 2 618 150 A1 | 7/2013 |
| EP | 2 618 151 A1 | 7/2013 |
| WO | WO 03/103835 A1 | 12/2003 |
| WO | WO 2005/089082 A2 | 9/2005 |
| WO | WO 2005/118139 A1 | 12/2005 |
| WO | WO 2006/080021 A2 | 8/2006 |
| WO | WO 2006/137785 A1 | 12/2006 |
| WO | WO 2007/012975 A1 | 2/2007 |
| WO | WO 2007/149042 A1 | 12/2007 |
| WO | WO 2007/149043 A1 | 12/2007 |
| WO | WO 2008/025945 A1 | 3/2008 |
| WO | WO2010/112833 * | 10/2010 |

OTHER PUBLICATIONS

Chinese Office Action and Search Report for CN 201410048800.0; dated Nov. 16, 2016; 12 pages.
U.S. Appl. No. 13/744,617, filed Jan. 18, 2013; Title: Low Volume Assay Device Having Increased Sensitivity; 44 pages.
U.S. Appl. No. 13/744,442, filed Jan. 18, 2013; Title: Assay Device Having Multiple Reagent Cells; 50 pages.
U.S. Appl. No. 13/744,641, filed Jan. 18, 2013; Title: Controlling Fluid Flow Through an Assay Device; 42 pages.
U.S. Appl. No. 14/081,158, filed Nov. 15, 2013; Title: Calibrating Assays Using Reaction Time; 57 pages.
Chinese Office Action for CN 201410048800.0; dated May 19, 2017; 11 pages.
European Office Action for EP 14 154 484.1; dated Jun. 26, 2017; 5 pages.

* cited by examiner

Fig. 7A
POC-EXP0982 Times to Start of WZ PCT P2 Serum

Fig. 7B
POC-EXP0982 Times to End of WZ PCT P2 Serum

REAGENT ZONE DEPOSITION PATTERN

CROSS REFERENCE TO RELATED APPLICATIONS

This patent application claims priority to U.S. Provisional Application No. 61/763,662, filed Feb. 12, 2013, the disclosure of which is incorporated by reference in its entirety.

FIELD OF THE INVENTION

The present invention relates to the field of diagnostic assays, and in particular to lateral flow assays where an analyte to be detected is present in a biological sample.

BACKGROUND

Diagnostic assays are widespread and central for the diagnosis, treatment and management of many diseases. Different types of diagnostic assays have been developed over the years in order to simplify the detection of various analytes in clinical samples such as blood, serum, plasma, urine, saliva, tissue biopsies, stool, sputum, skin or throat swabs and tissue samples or processed tissue samples. These assays are frequently expected to give a fast and reliable result, while being easy to use and inexpensive to manufacture. Understandably it is difficult to meet all these requirements in one and the same assay. In practice, many assays are limited by their speed. Another important parameter is sensitivity. Recent developments in assay technology have led to increasingly more sensitive tests that allow detection of an analyte in trace quantities as well the detection of disease indicators in a sample at the earliest time possible.

A common type of disposable assay device includes a zone or area for receiving the liquid sample, a conjugate zone also known as a reagent zone, and a reaction zone also known as a detection zone. These assay devices are commonly known as lateral flow test strips. They employ a porous material, e.g., nitrocellulose, defining a path for fluid flow capable of supporting capillary flow. Examples include those shown in U.S. Pat. Nos. 5,559,041, 5,714,389, 5,120,643, and 6,228,660 all of which are incorporated herein by reference in their entireties.

The sample-addition zone frequently consists of a more porous material, capable of absorbing the sample, and, when separation of blood cells is desired, also effective to trap the red blood cells. Examples of such materials are fibrous materials, such as paper, fleece, gel or tissue, comprising e.g. cellulose, wool, glass fiber, asbestos, synthetic fibers, polymers, or mixtures of the same.

WO 2007/012975 discloses a hybrid device that includes a capillary channel having bifurcations that is stated to help present a more united fluid front to the resuspension chamber, and thereby increase the speed of detection of a substance and improve the accuracy of detected results. US 2009/0311805 discloses an assay device having deposited conjugate in a conjugate zone. U.S. Pat. No. 6,271,040 discloses an assay device having a reaction chamber 4 that includes dried or lyophilized powders. The shape of the reaction chamber is disclosed as being such that the movement of the reaction mixtures from the reaction chamber is not turbulent and eddies are not formed as a result of the movement out of the reaction chamber.

Another type of assay device is a non-porous assay having projections to induce capillary flow. Examples of such assay devices include the open lateral flow device as disclosed in WO 2003/103835, WO 2005/089082, WO 2005/118139, and WO 2006/137785, all of which are incorporated herein by reference in their entireties.

US 2009/0311805 discloses an assay device having projections to induce capillary flow. The '805 application also discloses that a substance (i.e., reagent material) can be deposited between the projections in a substrate zone and can be dissolved by sample flowing through the substrate zone. The '805 application further discloses that the shape of the zone where the substance is applied, can be adapted to control the dissolution rate and/or how the dissolved substance is distributed in the flow of liquid sample. The '805 application further provides examples of shapes that can include a triangle, a square, a rectangle, a parallelogram, a rhombus, a trapezoid, a quadrilateral, a polygon, a circle, an oval, and truncated shapes such as a half circle, a half oval, a half polygon, and a circle segment.

Figure 1:
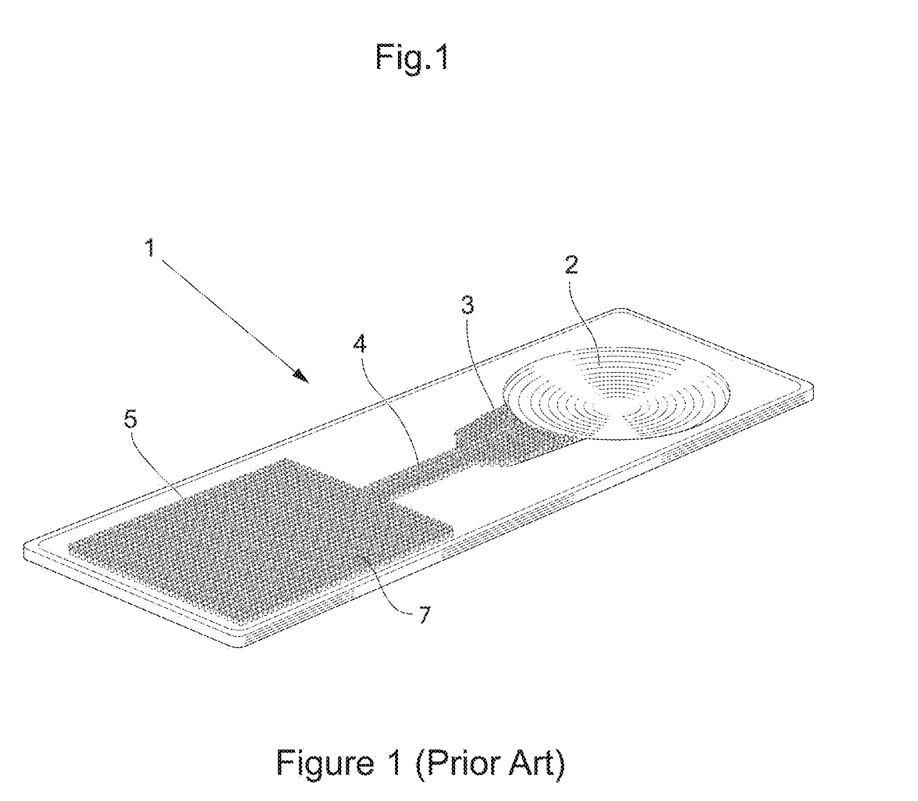
FIG. 1 shows a known assay device.

A known non-porous assay device is shown in FIG. 1. The assay device 1 has at least one sample addition zone 2, a reagent zone 3, at least one detection zone 4, and at least one wicking zone 5. The zones form a flow path by which sample flows from the sample addition zone to the wicking zone. Also included are capture elements, such as antibodies, in the detection zone 4, capable of binding to the analyte, optionally deposited on the device (such as by coating); and a labeled conjugate material also capable of participating in reactions that will enable determination of the concentration of the analyte, deposited on the device in the reagent zone, wherein the labeled conjugate material carries a label for detection in the detection zone. The conjugate material is dissolved as the sample flows through the reagent zone forming a conjugate plume of dissolved labeled conjugate material and sample that flows downstream to the detection zone. As the conjugate plume flows into the detection zone, the conjugated material will be captured by the capture elements such as via a complex of conjugated material and analyte (as in a "sandwich" assay) or directly (as in a "competitive" assay. Unbound dissolved conjugate material will be swept past the detection zone into the at least one wicking zone 5.

An instrument such as that disclosed in US 20060289787A1, US20070231883A1, U.S. Pat. No. 7,416,700 and U.S. Pat. No. 6,139,800 all incorporated by reference in their entireties is able to detect the bound conjugated analyte and label in the reaction zone. Common labels include fluorescent dyes that can be detected by instruments which excite the fluorescent dyes and incorporate a detector capable of detecting the fluorescent dyes. Such instruments have a read window that has a width that is typically on the order of 1 mm, which is a generally sufficient width to read enough signal, subject to an adequate width of the conjugate plume.

One drawback with such known assay devices such as those described above, is that the dissolved conjugate stream in the reaction zone is often narrower than the read window of the instrument, which may negatively impact assay sensitivity and variability. This is of particular concern for designs such as those described above where the conjugate material is deposited in the center of the conjugate zone and is dissolved from the sides as sample is flowing past. If the channel is made wider than the read window, although the dissolved reagent width may match the read window size, the fluid sample outside the read window contributes no signal and is wasted. Another drawback is that the dissolved reagent is not adequately mixed with the sample by the time it reaches the reaction zone, with the result being a lower signal in the middle of the reaction zone because dissolved reagent has local higher concentration and needs to diffuse to mix with sample further away from the reagent, and to bind with the analyte, and hence less signal being read by the read window of the instrument.

The sample size for such typical assay devices as shown in FIG. 1 are generally on the order of 200 µl. Such a sample size requires a venous blood draw from a medical professional such as a phlebotomist. There is an increasing need for lateral flow devices that are able to function with a much smaller sample size to accommodate the amount of blood available from a so-called "fingerstick" blood draw, which is on the order of 25 µl or less. Such a small amount of sample is the amount of blood in a drop of blood after pricking a fingertip with a lancet. Home blood glucose meters typically use a drop of blood obtained in such a fashion to provide glucose levels in blood. Such a smaller sample size would not require a medical professional to draw the blood and would provide greater comfort to the patients providing the sample for analysis.

To reduce the sample size required, the dimensions of the lateral flow assay devices are reduced to accommodate the smaller sample size. However, it has been found that reducing the sample size and dimensions of the device provides inadequate conjugate in the detection zone and accordingly less signal that can be read by the instrument. The inadequate conjugate in the detection zone is believed to be due to reduced sample size and inefficient use of the sample in the device, amongst other conditions. Another drawback of reducing dimensions is that the width of the detection zone will also be reduced, again making less signal available that can be read by the instrument.

Accordingly, there is a need for an assay device that can provide a wider reagent plume in the detection zone, better mix the dissolved reagent and sample, and make more efficient use of sample in an assay device, particularly in those devices where the conjugate material is deposited in the center of the conjugate zone and is dissolved from the sides.

SUMMARY OF THE INVENTION

The present invention is directed to an assay device that alleviates one or more the foregoing problems described above.

One aspect of the invention is directed to an assay device that includes: a liquid sample zone; a reagent zone downstream and in fluid communication with the sample zone. The reagent zone includes a reagent cell having a line of symmetry in the direction of fluid flow; and a reagent material in the reagent cell. The reagent material includes a first reagent material located at the axis of symmetry and is left-right symmetric, and a second and third reagent material having a substantially identical shape and volume and located in mirror locations from the line of symmetry; a detection zone in fluid communication with the reagent zone. The device further includes a wicking zone in fluid communication with the detection zone having a capacity to receive liquid sample flowing from the detection zone. The sample addition zone, the detection zone and the wicking zone define a fluid flow path.

Another aspect of the invention is directed to a method of increasing the width of a reagent plume flowing from a reagent zone and into a detection zone in an assay device. The method includes: providing a liquid sample zone; and providing a reagent zone downstream and in fluid communication with the sample zone. The reagent zone includes a reagent cell having a line of symmetry in the direction of fluid flow. The method further includes: providing a reagent material in the reagent cell, wherein the reagent material includes a first reagent material located at the axis of symmetry and is left-right symmetric, and a second and third reagent material having a substantially identical shape and volume and located in mirror locations from the line of symmetry; providing a detection zone in fluid communication with the reagent zone; and providing a wicking zone in fluid communication with the capture zone having a capacity to receive liquid sample flowing from the capture zone. The sample zone, the detection zone and the wicking zone define a fluid flow path. The method further includes adding sample to the sample zone; flowing the sample from the sample zone and into the reagent zone and past the first, second and third reagent materials. Sample flowing past the second and third reagent materials forms second and third reagent plumes along the edges of the reagent cell, and sample flowing past the first reagent material forms a first reagent plume along the line of symmetry of the reagent cell. The sample is flowed past the first, second and third reagent materials, such that the first, second and third reagent plume combine to form a combined reagent plume.

According to another aspect of the invention, there has been provided a method of performing an assay on a liquid sample for the presence or concentration of one or more analyte(s) or control(s), on the assay device described above. The method includes: depositing a liquid sample containing the analyte(s) of interest onto a sample addition zone of the assay device; moving the sample by capillary action through a fluid flow path into a reagent zone where it dissolves one or more reagents; flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and reading the signal(s) that are produced in the detection zones to determine the presence or concentration of the analytes or controls.

Further objects, features and advantages of the present invention will be apparent to those skilled in the art from detailed consideration of the preferred embodiments that follow.

DETAILED DESCRIPTION OF PREFERRED EMBODIMENTS

As used in this specification and the appended claims, the singular forms "a", "an" and "the" include plural referents unless the context clearly dictates otherwise.

The term "about" as used in connection with a numerical value throughout the description and the claims denotes an interval of accuracy, familiar and acceptable to a person skilled in the art. The interval is preferably ±10%.

The term "sample" herein means a volume of a liquid, solution or suspension, intended to be subjected to qualitative or quantitative determination of any of its properties, such as the presence or absence of a component, the concentration of a component, etc. Typical samples in the context of the present invention are human or animal bodily fluids such as blood, plasma, serum, lymph, urine, saliva, semen, amniotic fluid, gastric fluid, phlegm, sputum, mucus, tears, stool, etc. Other types of samples are derived from human or animal tissue samples where the tissue sample has been processed into a liquid, solution, or suspension to reveal particular tissue components for examination. The embodiments of the present invention are applicable to all bodily samples, but preferably to samples of whole blood, urine or sputum.

In other instances, the sample can be related to food testing, environmental testing, bio-threat or bio-hazard testing, etc. This is only a small example of samples that can be used in the present invention.

In the present invention, the determination based on lateral flow of a sample and the interaction of components present in the sample with reagents present in the device or added to the device during the procedure and detection of such interaction, either qualitatively or quantitatively, may be for any purpose, such as diagnostic purposes. Such tests are often referred to as lateral flow assays.

Examples of diagnostic determinations include, but are not limited to, the determination of analytes, also called markers, specific for different disorders, e.g. chronic metabolic disorders, such as blood glucose, blood ketones, urine glucose (diabetes), blood cholesterol (atherosclerosis, obesity, etc); markers of other specific diseases, e.g. acute diseases, such as coronary infarct markers (e.g. troponin-T, NT-ProBNP), markers of thyroid function (e.g. determination of thyroid stimulating hormone (TSH)), markers of viral infections (the use of lateral flow immunoassays for the detection of specific viral antibodies); etc.

Yet another important field is the field of companion diagnostics where a therapeutic agent, such as a drug, is administered to an individual in need of such a drug. An appropriate assay is then conducted to determine the level of an appropriate marker to determine whether the drug is having its desired effect. Alternatively, the assay device of the present invention can be used prior to administration of a therapeutic agent to determine if the agent will help the individual in need.

Yet another important field is that of drug tests, for easy and rapid detection of drugs and drug metabolites indicating drug abuse; such as the determination of specific drugs and drug metabolites (e.g. THC) in urine samples etc.

The term "analyte" is used as a synonym of the term "marker" and intended to encompass any chemical or biological substance that is measured quantitatively or qualitatively and can include small molecules, proteins, antibodies, DNA, RNA, nucleic acids, virus components or intact viruses, bacteria components or intact bacteria, cellular components or intact cells and complexes and derivatives thereof.

The terms "zone", "area" and "site" are used in the context of this description, examples and claims to define parts of the fluid flow path on a substrate, either in prior art devices or in a device according to an embodiment of the invention.

The term "reaction" is used to define any reaction, which takes place between components of a sample and at least one reagent or reagents on or in the substrate, or between two or more components present in the sample. The term "reaction" is in particular used to define the reaction, taking place between an analyte and a reagent as part of the qualitative or quantitative determination of the analyte.

The term "substrate" means the carrier or matrix to which a sample is added, and on or in which the determination is performed, or where the reaction between analyte and reagent takes place.

Figure 2:
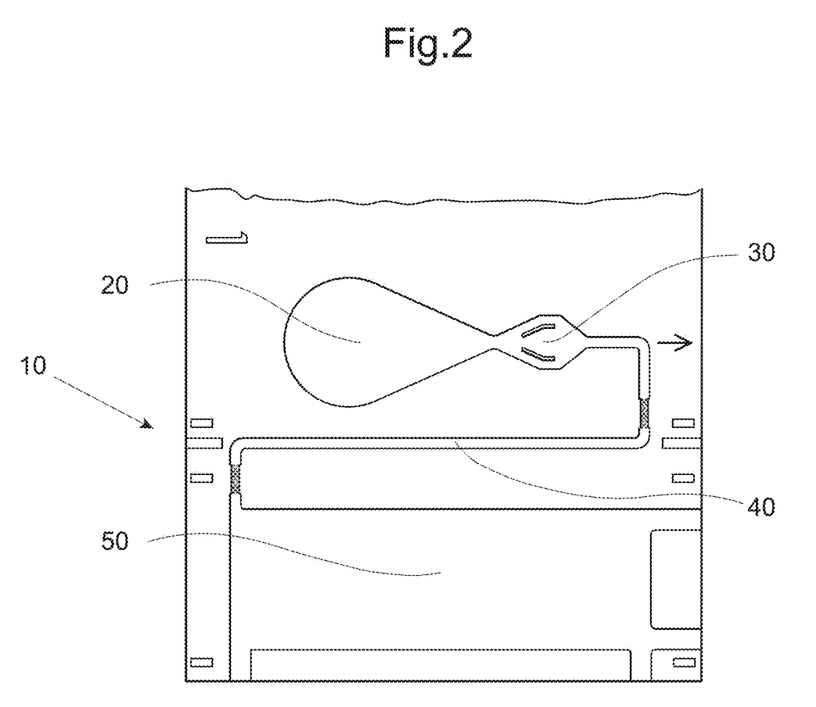
FIG. 2 shows a schematic view of an assay device usable with the present invention.

The present invention is directed to a lateral flow assay device for determining the presence or amount of at least one analyte that solves, at least in part, the problem of lowered signal due to a narrow reagent plume or reduced sample size. FIG. 2 shows a schematic view of a preferred embodiment of such a device according to the invention. The assay device 10 has at least one sample zone (also referred to as sample addition zone) 20, at least one reagent zone 30, at least one detection zone 40, and at least one wicking zone 50. The zones form a flow path by which sample flows from the sample addition zone to the wicking zone.

Components of the assay device (i.e., a physical structure of the device whether or not a discrete piece from other parts of the device) can be prepared from copolymers, blends, laminates, metalized foils, metalized films or metals. Alternatively, device components can be prepared from copolymers, blends, laminates, metalized foils, metalized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials. Alternatively, components of the device are made with a plastic, elastomer, latex, silicon chip, or metal; the elastomer can comprise polyethylene, polypropylene, polystyrene, polyacrylates, silicon elastomers, or latex. Alternatively, components of the device can be prepared from latex, polystyrene latex or hydrophobic polymers; the hydrophobic polymer can comprise polypropylene, polyethylene, or polyester. Alternatively, components of the device can comprise TEFLON®, polystyrene, polyacrylate, or polycarbonate. Alternatively, device components are made from plastics which are capable of being embossed, milled or injection molded or from surfaces of copper, silver and gold films upon which may be adsorbed various long chain alkanethiols. The structures of plastic which are capable of being milled or injection molded can comprise a polystyrene, a polycarbonate, or a polyacrylate. In a particularly preferred embodiment, the assay device is injection molded from a cyclo olefin polymer, such as those sold under the name Zeonor®. Preferred injection molding techniques are described in U.S. Pat. Nos. 6,372,542, 6,733,682, 6,811,736, 6,884,370, and 6,733,682, all of which are incorporated herein by reference in their entireties.

The flow path can include open or closed paths, grooves, and capillaries. Preferably the flow path comprises a lateral flow path of adjacent projections, having a size, shape and mutual spacing such that capillary flow is sustained through the flow path. In one embodiment, the flow path is in a channel within the substrate having a bottom surface and side walls. In this embodiment, the projections protrude from the bottom surface of the channel. The side walls may or may not contribute to the capillary action of the liquid. If the sidewalls do not contribute to the capillary action of the liquid, then a gap can be provided between the outermost projections and the sidewalls to keep the liquid contained in the flow path defined by the projections. FIG. 1 shows projections 7.

In one embodiment the flow path is at least partially open. In another embodiment the flow path is entirely open. Open means that there is no lid or cover at a capillary distance. Thus the cover, if present as a physical protection for the flow path, does not contribute to the capillary flow in the flow path. An open lateral flow path is described for example in the following published applications: WO 2003/103835, WO 2005/089082; WO 2005/118139; WO 2006/137785; and WO 2007/149042, all of which are incorporated by reference in their entireties. The projections have a height (H), diameter (D) and a distance or distances between the projections (t1, t2) such, that lateral capillary flow of the fluid, such as plasma, preferably human plasma, in the zone is achieved. These dimensions are shown in US 2006/0285996, which is incorporated by reference in its entirety. In addition to optimizing the above-mentioned height, diameter and a distance or distances between the projections, the projections may be given a desired chemical, biological or physical functionality, e.g. by modifying the surface of the projections. In one embodiment, the projections have a height in the interval of about 15 to about 150 µm, preferably about 30 to about 100 µm, a diameter of about 10 to about 160 µm, preferably 40 to about 100 µm, and a gap or gaps between the projections of about 3 to about 200 µm, preferably 5 to about 50 µm or 10 to 50 µm from each other. The flow channel may have a length of about 5 to about 500 mm, preferably about 10 to about 100 mm, and a width of about 0.3 to about 10 mm, preferably about 0.3 to about 3 mm, preferably about 0.5 to 1.5, and preferably about 0.5 to 1.2 mm.

While most detection will occur in the detection zone portion of the fluid flow path, it is also possible that detection may occur in other parts of the device. For example, non-invasive, non-reactive sample integrity measurements may occur between the sample zone and the reagent zone or reagent addition zone, preferably after a filter element, if present. Other measurements may include blanks reads, one part of a two part reaction sequence as for measuring both hemoglobin and glycated hemoglobin for determination of HbA1c, etc.

The liquid sample zone 20, also referred to as the liquid sample addition zone, receives sample from a sample dispenser, such as a pipette. The sample is typically deposited onto the top of the zone. The sample addition zone is capable of transporting the liquid sample from the point where the sample is deposited to the reagent zone, through an optional filter and reagent addition zone, preferably through capillary flow. The capillary flow inducing structure can include porous materials, such as nitrocellulose, or preferably through projections, such as micro-pillars, as shown in FIG. 1. In those devices that can use finger stick volumes of blood, the sample can be directly touched off from the finger, or by a capillary pipette.

A filter material (not shown) can be placed in the sample addition zone to filter particulates from the sample or to filter blood cells from blood so that plasma can travel further through the device.

Located between the sample addition zone and the detection zone is a reagent zone 30. The reagent zone can include reagent material(s) integrated into the analytical element and are generally reagents useful in the reaction—binding partners such as antibodies or antigens for immunoassays, substrates for enzyme assays, probes for molecular diagnostic assays, or are auxiliary materials such as materials that stabilize the integrated reagents, materials that suppress interfering reactions, etc. Generally one of the reagents useful in the reaction bears a detectable signal as discussed below. In some cases the reagents may react with the analyte directly or through a cascade of reactions to form a detectable signal such as, but not restricted to, a molecule detectable using spectroscopy such as a colored or fluorescent molecule. In one preferred embodiment, the reagent zone includes conjugate material. The term conjugate means any moiety bearing both a detection element and a binding partner.

The detection element is an agent which is detectable with respect to its physical distribution or/and the intensity of the signal it delivers, such as but not limited to luminescent molecules (e.g. fluorescent agents, phosphorescent agents, chemiluminescent agents, bioluminescent agents and the like), colored molecules, molecules producing colors upon reaction, enzymes, radioisotopes, ligands exhibiting specific binding and the like. The detection element also referred to as a label is preferably chosen from chromophores, fluorophores, radioactive labels, and enzymes. Suitable labels are available from commercial suppliers, providing a wide range of dyes for the labeling of antibodies, proteins, and nucleic acids. There are, for example, fluorophores spanning practically the entire visible and infrared spectrum. Suitable fluorescent or phosphorescent labels include for instance, but are not limited to, fluoresceins, Cy3, Cy5 and the like. Suitable chemoluminescent labels are for instance but are not limited to luminol, cyalume and the like.

Similarly, radioactive labels are commercially available, or detection elements can be synthesized so that they incorporate a radioactive label. Suitable radioactive labels are for instance but are not limited to radioactive iodine and phosphorus; e.g. $^{125}I$ and $^{32}P$.

Suitable enzymatic labels are, for instance, but are not limited to, horseradish peroxidase, beta-galactosidase, luciferase, alkaline phosphatase and the like. Two labels are "distinguishable" when they can be individually detected and preferably quantified simultaneously, without significantly disturbing, interfering or quenching each other. Two or more labels may be used, for example, when multiple analytes or markers are being detected.

The binding partner is a material that can form a complex that can be used to determine the presence of or amount of an analyte. For example, in an "sandwich" assay, the binding partner in the conjugate can form a complex including the analyte and the conjugate and that complex can further bind to another binding partner, also called a capture element, integrated into the detection zone. In a competitive immunoassay, the analyte will interfere with binding of the binding partner in the conjugate to another binding partner, also called a capture element, integrated into the detection zone. Example binding partners included in conjugates include antibodies, antigens, analyte or analyte-mimics, protein, etc.

Optionally located in the fluid flow path, before or after the reagent zone and before the detection zone is a reagent addition zone. The reagent addition zone is shown as 35 in FIG. 3. The reagent addition zone can allow addition of a reagent externally from the device. For example, the reagent addition zone may be used to add an interrupting reagent that may be used to wash the sample and other unbound components present in the fluid flow path into the wicking zone. In a preferred embodiment the reagent addition zone 35 is located after the reagent zone 30.

Downstream from the liquid sample zone and the reagent zone is the detection zone 40 which is in fluid communication with the sample addition zone. The detection zone 40 may include projections such as those described above. As also noted above, these projections are preferably integrally molded into the substrate from an optical plastic material such as Zeonor, such as injection molding or embossing. The width of the flow channel in the detection zone is typically on the order of 2 mm for conventional size devices, however, some lower volume devices, such as those described above and in co pending application entitled "Lower Volume Assay Device Having Increased Sensitivity," Ser. No. 13/744,617, filed on Jan. 20, 2013 and incorporated by reference in its entirety, are significantly narrower, e.g., 1.5 mm or less, preferably 0.5 to 1.2 mm.

The detection zone is where any detectable signal is read. In a preferred embodiment attached to the projections in the detection zone are capture elements. The capture elements can include binding partners for the conjugate or complexes containing the conjugate, as described above. For example, if the analyte is a specific protein, the conjugate may be an antibody that will specifically bind that protein coupled to a detection element such as a fluorescence probe. The capture element could then be another antibody that also specifically binds to that protein. In another example, if the marker or analyte is DNA, the capture molecule can be, but is not limited to, synthetic oligonucleotides, analogues thereof, or specific antibodies. Other suitable capture elements include antibodies, antibody fragments, aptamers, and nucleic acid sequences, specific for the analyte to be detected. A non-limiting example of a suitable capture element is a molecule that bears avidin functionality that would bind to a conjugate containing a biotin functionality. The detection zone can include multiple detection zones. The multiple detection zones can be used for assays that include one or more markers. In the event of multiple detection zones, the capture elements can include multiple capture elements, such as first and second capture elements. The conjugate can be pre-deposited on the assay device, such as by coating in the reagent zone. Similarly the capture elements can be pre-deposited on the assay device on the detection zone. Preferably, both the detection and capture elements are pre-deposited on the assay device, on the detection zone and detection zone, respectively.

After the sample has been delivered to the sample zone, it will encounter the reagent zone. After the sample has flowed through and interacted with the reagent zone and optionally the reagent addition zone, the sample and a reagent plume will be contained in the fluid flow. The reagent plume can contain any of the reagent materials that have been dissolved in the detection zone or those added through the reagent addition zone. The reagent in the sample flowing from the reagent zone is considered to be a reagent plume. The reagent plume can include the conjugate having both the detection element and binding partner, in which case it is often referred to as a conjugate plume. As noted throughout, a challenge facing the inventor was to keep the reagent plume as wide as possible as it enters the detection zone.

Fluid flow through an assay device, including the reagent zone, is generally laminar as opposed to turbulent flow. In laminar flow, mixing is achieved mostly by diffusion of the solute (i.e., reagent material) through the fluid (i.e., sample) which is a slow process. In a reagent zone of a conventional assay device, a single area of reagent material is located in the center of the reagent zone. Upstream sample fluid flowing from the sample addition zone in a laminar manner contacts the material and separates into two different flow streams that flow along the sides of the material. Because of the laminar flow, there is a high concentration of the dissolved material in the sample fluid at the fluid/reagent material interface, and a low concentration of the dissolved material in the fluid at points that are only a short distance from the interface. Also, in view of the relatively short time the sample fluid is flowing through the assay system, there is insufficient diffusion of the material throughout the fluid. As a result, when the fluid streams recombine after flowing around the reagent material in the reagent zone, the bulk of the dissolved/suspended reagent material is located mainly in the center of the fluid flow path, leading to the issues of inefficient use of sample (i.e., the sample that has no or insufficient concentration of material being essentially wasted) and less than desirable sensitivity.

One solution to the problem of insufficiently wide reagent plume is described in co-pending application entitled "Assay Device Having Multiple Reagent Cells," Ser. No. 13/744,442 filed on Jan. 18, 2013, which uses multiple reagent cells within the reagent zone, and is incorporated by reference in its entirety. However, in some instances it would be desirable to employ a single reagent cell, as opposed to multiple reagent cells.

The present invention is based, in part, on the surprising discovery that an assay device such as those described herein which employs multiple segmented reagent materials, positioned relative to each other and relative to the sample flow, within a single reagent cell, such that the sample flow through the conjugate cell is brought into intimate contact with the reagent materials, is able to produce reagent plume exiting the reagent cell extends across a significant portion of the fluid flow path, preferably substantially the entire width of the fluid flow path. Thus, with a single reagent cell it may be possible to produce a reagent plume having a width in the fluid flow path that rivals that of a reagent plume produced by multiple reagent cells, such as those described in the copending application above.

Figure 4A:
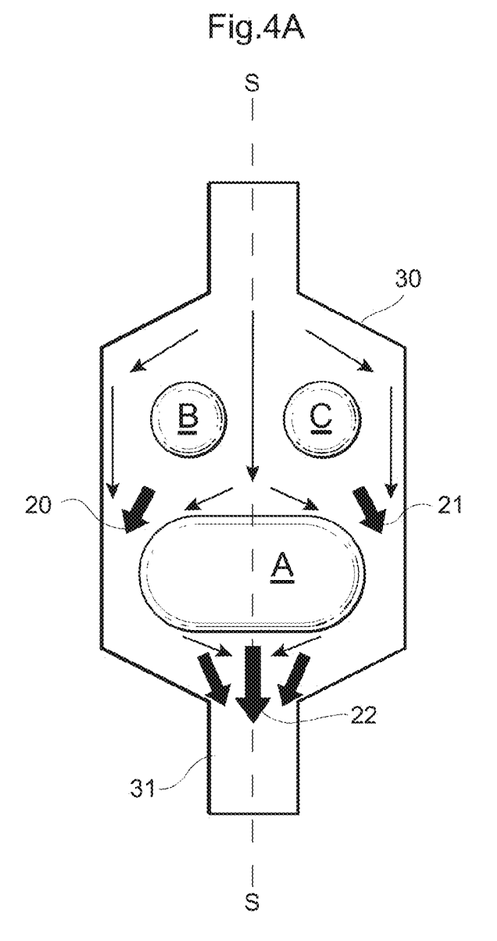
FIGS. 4A and 4B shows schematic views of a reagent zone of an assay device having reagent material deposited therein according to preferred embodiments of the invention.
Figure 4B:
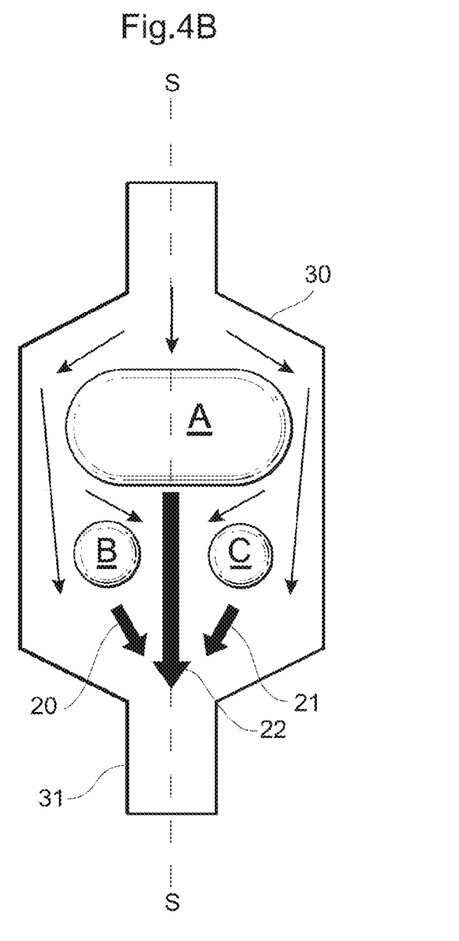

An important feature of the invention is the number, size and location of the multiple reagent materials, i.e., segments, with regards to each other and the flow of sample through the reagent zone. More specifically, the reagent cell 30 includes an axis of symmetry S that substantially equally divides the cell in the direction of flow of the sample as shown in FIGS. 4A and 4B. A first reagent material A is located in the reagent cell such that the axis of symmetry S bisects the material A with approximately equal halves of the material A being located on both sides of the line S. In other words each half is a substantially mirror image of each other.

In addition to the first reagent material A, there is also second and third segment reagent materials B and C. The position of these materials in the reagent cell is important to ensuring a uniform, wide reagent plume. Specifically, these are located upstream or downstream of the material A. Also they are located on both sides of the line of symmetry S such that they left-right symmetric. While it is not necessary that they are the same exact shape, they should have the same dissolution characteristics, such that they dissolve at substantially the same rate and substantially completely dissolve at the same time. Preferably, the materials B and C are identical and are mirror images of each other when viewed from line S.

The size of either the area or the total volume of the material A segment and its location relative to materials B and C segments should be such that it dissolves either at the same time as materials B and C, or is the last to be completely dissolved. In a preferred embodiment, the ratio of the size of material A to each of materials B and C is in the range of 3:1 to 2:1.

This shape of the materials can be selected to give a desired dissolution profile. Preferably, the material A has an oval or elliptical shape, with the long axis perpendicular to the direction of flow, as shown in the figures. Materials B and C are preferably substantially circular in shape. However, other shapes can be selected based on the profile of the desired reagent plume which flows out of the reagent zone. Materials B and C are preferably substantially identical in shape.

The composition of the reagent materials A, B and C can be the same or different. For example, the materials A, B and C can have the same composition. Alternatively, material A can have one composition and materials B and C can have the same composition, but be different than material A's composition.

As described above, in those embodiments where micropillars are used to generate flow in the reagent zone, the reagent materials are preferably deposited on the substrate in liquid form, such as by ink jet printing, and allowed to dry. Upon drying, the height of the reagent material for all materials A, B and C will be preferably substantially the same, and may fill the spaces between the micropillars up to substantially the tops of the micropillars in the reagent zone.

FIGS. 4A and B shows the arrangement of the reagent materials and flow streams according to two preferred embodiments. As shown in both FIGS. 4A and B, material A is the larger one and is left-right symmetric. It is located at the symmetry axis S of the reagent cell. The reagent plume formed by the flow of fluid past material A will be at the middle of the cell. Materials B and C are smaller than material A. In both embodiments, the materials B and C are substantially identical in size and dissolution characteristics. They are separated and located symmetrically by the axis of symmetry S in the flow cell upstream of material A as shown in FIG. 4A or downstream as shown in FIG. 4B. The FIG. 4A embodiment is called a reverse segmented reagent cell and FIG. 4A is called a segmented reagent cell.

As shown in FIGS. 4A and B, the thin arrows represent sample fluid velocity vectors as fluid flows through the reagent cell 30. The thick arrows represent the reagent plumes flowing from their respective reagent materials. It is important that sufficient spaces are provided between the reagent materials B and C such that fluid flows between the reagent material segments. The separation between materials B and C will make the reagent plumes generated by materials B and C spread further away from the plume generated by material A (the center), which in turn, makes the total combined plume wider. On the other hand, if the separation between B and C is too large, there may be insufficient sample flow past materials B and C resulting in incomplete dissolution, especially if material A dissolves quickly. Materials B and C will form two reagent plumes 20 and 21 at the left and right side in the reagent cell, which thus, along with reagent plume 22 from material A, contributes to a reagent plume that extends across a greater width of the fluid flow path 31 than a reagent cell with a single reagent material deposition in the reagent cell.

In a particularly preferred embodiment, reagent material A is the last one to get completely dissolved since the deposited conjugate material A prevents fluid flowing across A along the symmetry line S and makes fluid flow by materials B and C. That will ensure the complete dissolution of the two conjugates.

If material A is dissolved earlier, the shortest streamline is along the axis of symmetry S which is far from material B and C. Flow near B and C is much slower since fluid tends to flow along the stream line in current flow cell design. That leads to a slow dissolution, or even no complete dissolution of the two conjugates.

With multiple reagent plumes, the combined reagent plume will be wider than a single reagent deposition, and may lead to increased sensitivity and reduce sample waste.

As described above, the reagent plume formed by the present invention is sufficiently wide that a single reagent cell may be successfully employed. However, the present invention can used equally well in those systems having multiple reagent cells such as described in the copending application described above and as shown in FIG. 3.

While the present invention, in particular the multiple reagent materials in a single reagent cell have been described with reference to non-porous projections, it is within the scope of the invention that the multiple reaction cells can be used on a nitrocellulose strip format or some other porous material. In one embodiment, the appropriate flow elements are formed via thermal means (i.e., melting the nitrocellulose with a heated die set forming the flow control elements) or with a printing technique where an insoluble barrier is laid down to form the flow paths and flow control elements.

Downstream from the detection zone is a wicking zone in fluid communication with the detection zone. The wicking zone is an area of the assay device with the capacity of receiving liquid sample and any other material in the flow path, e.g., unbound reagents, wash fluids, etc. The wicking zone provides a capillary force to continue moving the liquid sample through and out of the detection zone. The wicking zone can include a porous material such as nitrocellulose or can be a non-porous structure such as the projections described herein. The wicking zone can also include non-capillary fluid driving means, such as using evaporative heating or a pump. Further details of wicking zones as used in assay devices according to the present invention can be found in patent publications US 2005/0042766 and US 2006/0239859, both of which are incorporated herein by reference in their entireties. Wicking zones are also described in copending patent application entitled "Controlling Fluid Flow Through An Assay Device," Ser. No. 13/744,641, filed on Jan. 18, 2013, and incorporated by reference in its entirety.

Preferably the entirety of the flow path including the sample addition zone, the detection zone and the wicking zone includes projections substantially vertical in relation to the substrate, and having a height, diameter and reciprocal spacing capable of creating lateral flow of the sample in the flow path.

In any of the above embodiments, the device is preferably a disposable assay device. The assay device may be contained in a housing for ease of handling and protection. If the assay device is contained in such a housing, the housing will preferably include a port for adding sample to the assay device.

The assay device of the present invention can be used with a device for reading (a reader) the result of an assay device performed on the assay of the present invention. The reader includes means for reading a signal emitted by, or reflected from the detection element, such as a photodetector, and means for computing the signal and displaying a result, such as microprocessor that may be included within an integrated reader or on a separate computer. Suitable readers are described for example in US 2007/0231883 and U.S. Pat. No. 7,416,700, both of which are incorporated by reference in their entireties.

Another embodiment is a device for reading the result of an assay performed on an assay device, wherein the device comprises a detector capable of reading a signal emitted from or reflected from at least one detection element present in a defined location of the assay device. In either of the above embodiments, the reading preferably is chosen from the detection and/or quantification of color, fluorescence, radioactivity or enzymatic activity.

Another aspect of the invention is directed to a method of performing an assay on a liquid sample for the detection of one or more analytes of interest. A liquid sample containing the analyte(s) of interest is deposited onto the sample zone of the assay device, such as through a port in the housing of the device, or by touching off a finger directly onto the sample zone or a capillary in fluid communication with the sample zone in the case of a fingerstick blood draw. The sample moves by capillary action through an optional filter and into the reagent zone where it encounters the multiple reagent materials. The sample flows past the first, second and third reagent material. The reagent material flowing past the second and third reagent materials form second and third reagent plumes along the edges of the reagent cell. The sample flowing past the first reagent material forms a first reagent plume long the line of symmetry of the reagent cell. The first, second and third reagent material combine upon leaving the reagent cell to form a combined reagent plume.

Next the sample and reagent plume move by capillary action into the detection zone. There a signal representative of the presence or concentration of the analyte(s) or control is produced. In a preferred embodiment the sample or the one or more reagents having a detection element is captured having in the detection zone, such as by antibodies on the surface of the detection zone and a signal representative of the presence or concentration of the analyte(s) or control(s) is produced.

The reader as described above is then used to read the signal that is produced by the detection element to determine the presence or concentration of the analyte(s). The sample moves from the detection zone and into the wicking zone. The reader may read the signal immediately or a short time after the sample has moved through the detection zone. Also, one or more washes may follow the sample through the device to wash any unbound detection element away from the detection zone.

Example

Figure 3:
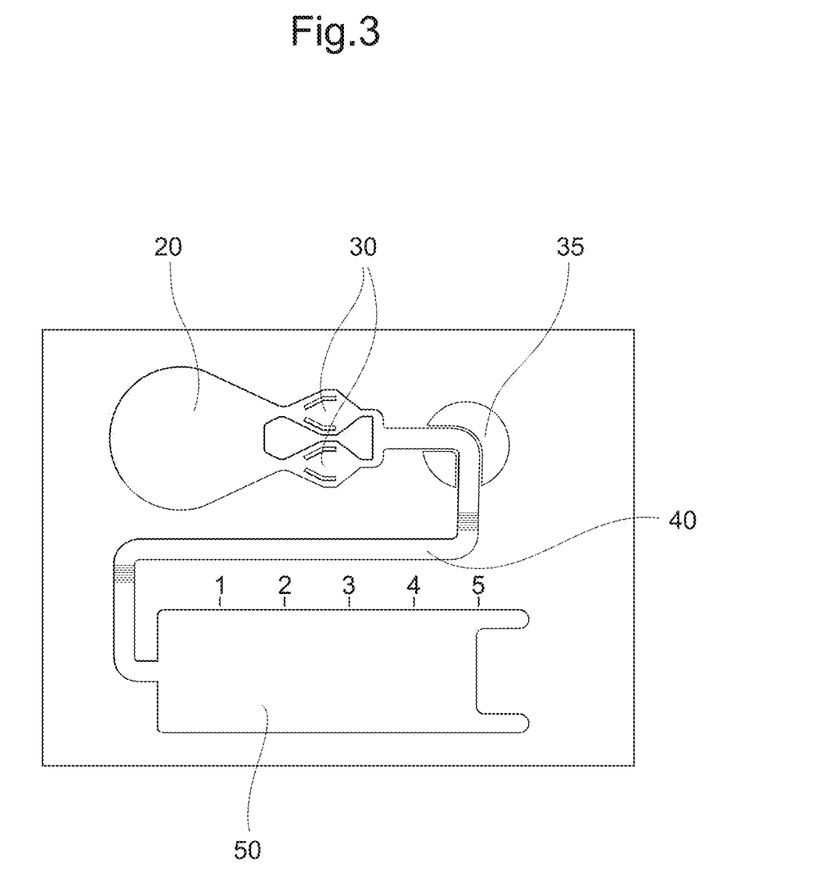
FIG. 3 shows a schematic view of an assay device usable with the present invention.

Plastic substrate chips made of Zeonor (Zeon, Japan) having oxidized dextran on the surface for covalently immobilization of proteins via Schiff base coupling were used. Fluorescently labeled Anti-procalcitonin (PCT) monoclonal antibody was deposited and dried to create a reagent zone. For the control having a single reagent cell (i.e., not a dual reagent cell such as shown in FIG. 3) 618 nL of the reagent material containing the antibody was deposited in one area. For the control having dual reagent cells 260 nL of the reagent material containing the antibody was deposited in one area in each of the cells for a total of 520 nL. For the segmented and reverse segmented reagent cells, a total of 618 nL of reagent was deposited approximately as shown in FIGS. 4B and 4A, respectively. Anti-PCT monoclonal antibody was deposited and dried to create a detection zone. A small amount of Triton X-45 was deposited on the device to increase wettability of the sample for better capillary flow. Sample having PCT in a concentration of 0.97 ng/ml was added to the sample zone of the device and the capillary action of the micropillar array distributed the sample through the flow channel into the wicking zone. The results of the Example are shown in FIGS. 5-7.

Figure 5A:
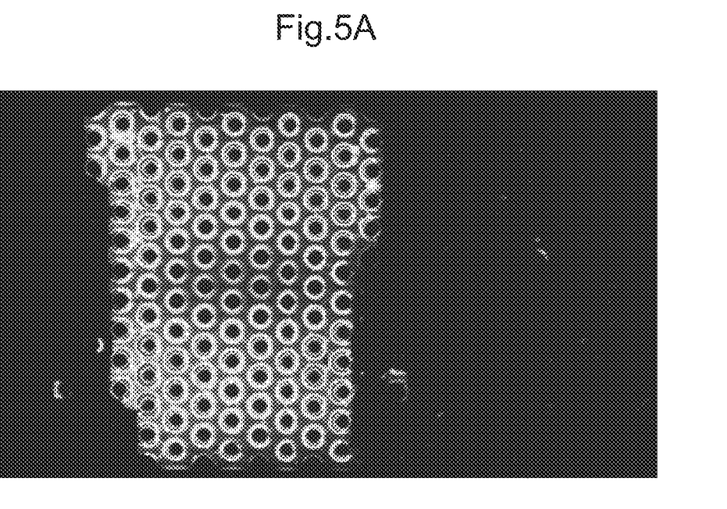
FIGS. 5A-5D are fluorescent microscope evaluation photographs showing the fluorescence emitted from fluorescent conjugate captured in the detection zone during assays conducted with assay devices with a bifurcated reagent zone, a segmented reagent zone, a reverse segmented reagent zone, and a control zone, respectively.
Figure 5B:
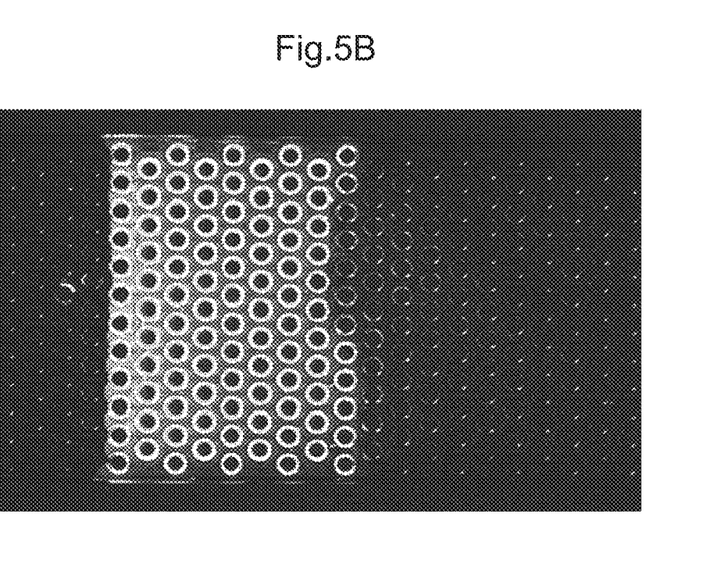
Figure 5C:
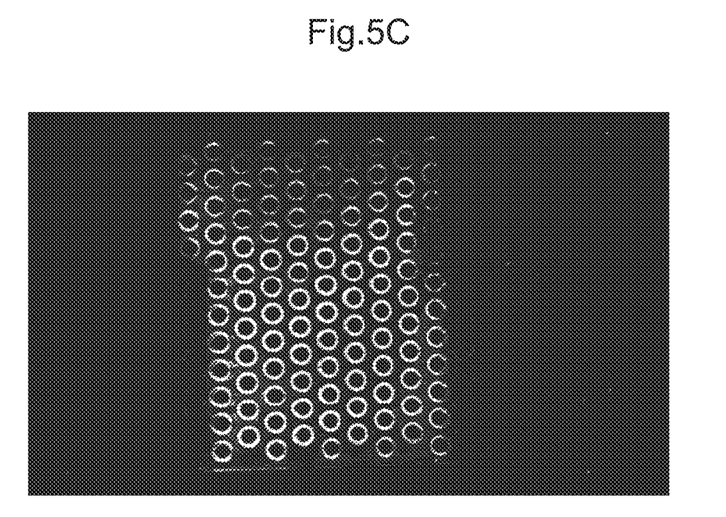
Figure 5D:
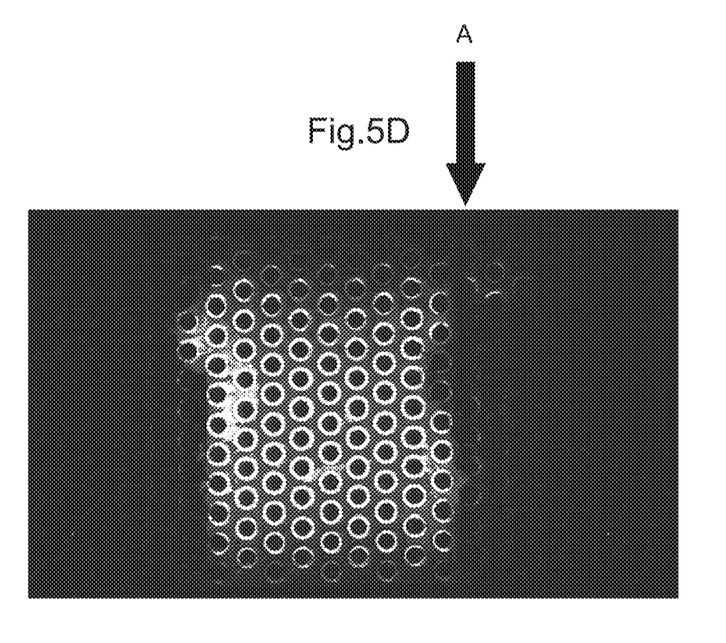

FIGS. 5A-5D are fluorescent microscope photographs showing micropillars in the flow path of the assay device following completion of an assay. The flow direction of the sample and reagent plume is left to right. The highlighted micropillars show where the fluorescently labeled anti-PCT conjugate complexed with PCT was captured by anti-PCT in the detection zone. Only micropillars in the detection zone around which reagent plume passed can capture the fluorescent conjugate-PCT complex. A larger number of micropillars in a cross-section of the detection zone that contain captured fluorescent conjugate-PCT complex thus indicates a wider reagent plume. A wider fluorescent pattern thus indicates a wider plume resulting in a more efficient use of the sample. In other words, a wider reagent plume means more sample is contributing to signal as opposed to merely passing through the system. FIG. 5A shows a first control device which includes dual reagent cells, as described in co-pending application entitled "Assay Device Having Multiple Reagent Cells," Ser. No. 13/744,442 filed on Jan. 18, 2013. As the microphotograph shows, the reagent plume extends over substantially the entire width of the flow path as evidenced by the entire width of micropillars in a row being highlighted. FIG. 5D shows another control device that includes a single reagent cell having the same dimensions as the reagent cell for the segmented and reverse segmented reagent deposition patterns according to the present invention. As FIG. 5D shows, the entire width of the flow channel is not highlighted. In fact, in the row shown by arrow A only 10 micropillars are clearly highlighted. FIG. 5B shows a microphotograph of device according to one embodiment of the present invention. In this figure, for most of the rows of micropillars highlighted all twelve micropillars (the entire flow path width) are clearly highlighted. FIG. 5C shows a microphotograph for another embodiment of the present invention. While the results are not as dramatic as the embodiment of FIG. 5B, many of the rows show all twelve micropillars in the row being clearly discernable.

Figure 6:
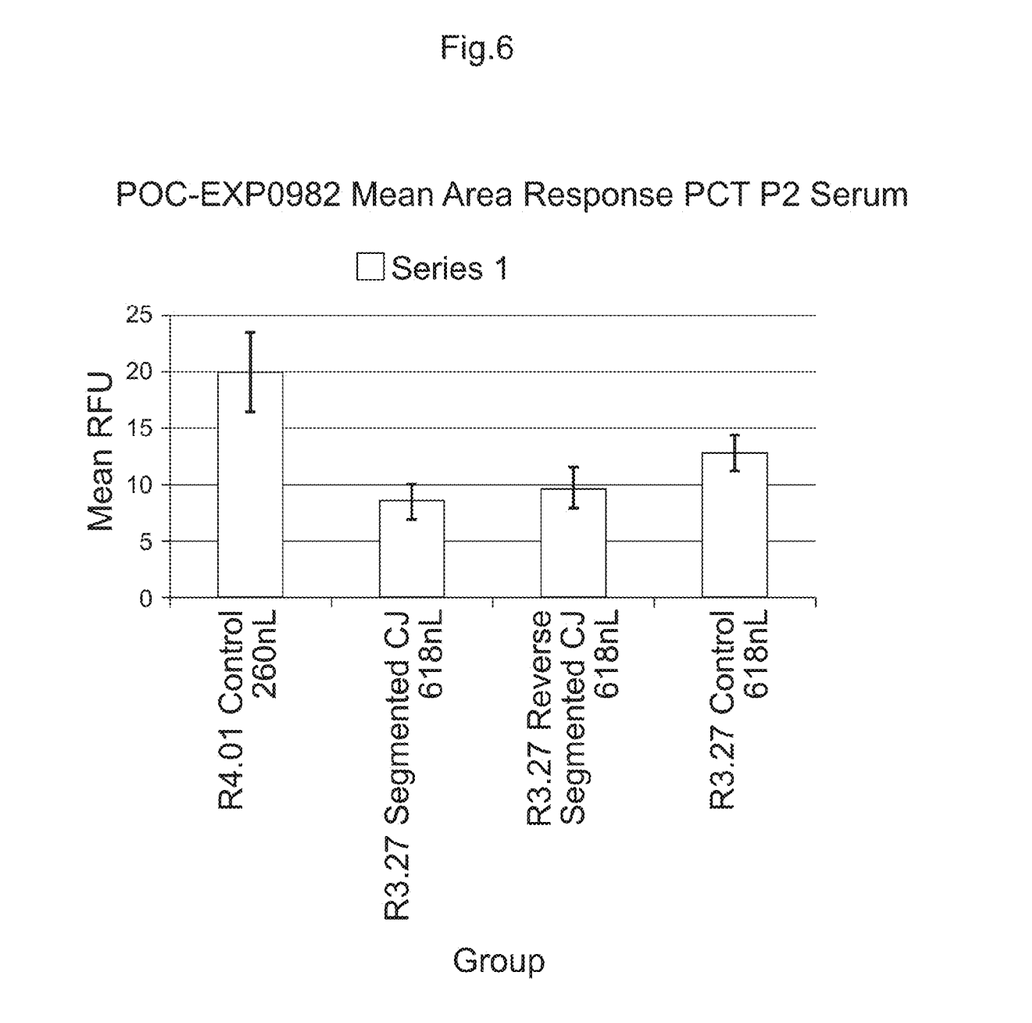
FIG. 6 shows the signal response from a segmented reagent zone as shown in FIG. 4B, from a reverse segmented conjugate zone as shown in FIG. 4A, from a bifurcated reagent zone and from a control reagent zone.

FIG. 6 shows the signal response for each of the four different devices described in reference to FIGS. 5A-5D. The far left bar graph is the dual reagent cell design and has the highest signal. The far right graph is the other control device that includes a single reagent cell having the same dimensions as the reagent cell for the segmented and reverse segmented reagent cells according to the present invention, but with a single deposition. The second and third bar graphs are the segmented and reverse segmented reagent cells, respectively. Although, the segmented and reverse segmented cells make much more efficient use of the flow stream as shown by the increased reagent plume width in FIGS. 5B and 5C than the control of FIG. 5D, the response as shown in FIG. 6 is actually less. This is believed to be because the response will depend on both the reagent plume width as well as the reaction time. The concept of reaction time is described in detail in copending application Ser. No. 14/081,158 filed Nov. 15, 2013 entitled "Calibrating Assays Using Reaction Time" and incorporated herein by reference in its entirety. Reaction time is dependent on reagent dissolution time. For the present invention the reagent dissolution times where in the range of from 3.5 to 5.5 minutes, whereas the reagent dissolution times for both controls was from 6 to 6.5 minutes, which is due to the much larger wet-dry interface made possible by the multiple reagent deposition patterns of the present invention. In order to increase reagent dissolution time and hence reaction time, the total amount of reagent deposited for the multiple reagent material reagent cells can be increased.

Figure 7A:
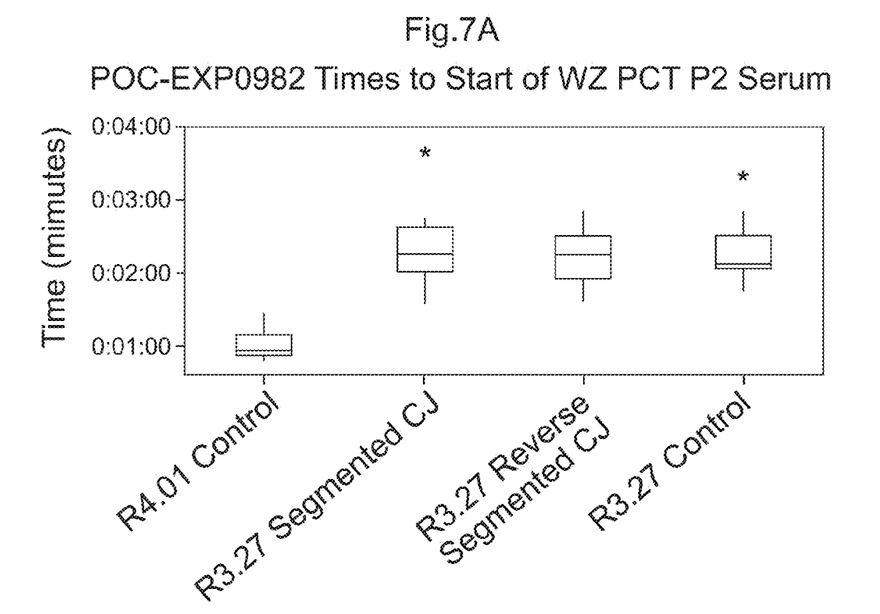
FIG. 7A shows the time to the beginning of the wicking zone for devices with a segmented reagent zone as shown in FIG. 4B, with a reverse segmented reagent zone as shown in FIG. 4A, with a bifurcated reagent zone, and with a control reagent zone.
Figure 7B:
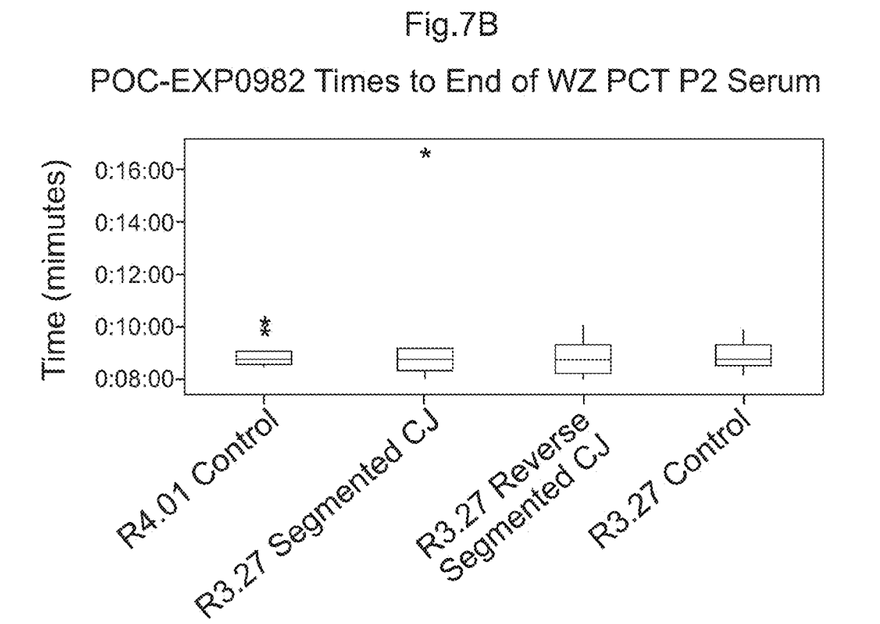
FIG. 7B shows the time to the end of the wicking zone for devices with a segmented reagent zone as shown in FIG. 4B, with a reverse segmented reagent zone as shown in FIG. 4A, with a bifurcated reagent zone, and with a control reagent zone.

Finally, FIGS. 7A and 7B show the times for the conjugate plume to reach the start and end of the wicking zones, respectively for each of the four different devices described in reference to FIGS. 5A-5D. This is an indicator of flow rate or total flow time. As FIGS. 7A and 7B show, the reagent distribution between those designs having an identical reagent cell does not appreciably affect total flow rate or flow time.

The method, assay device, and reader according to an embodiment of the invention have many advantages, mainly related to the improved detection kinetics of the immunochemical reactions and the increased sensitivity of the assay. It is to be understood that this invention is not limited to the particular embodiments shown here.

Additional Embodiments

An assay device comprising: a liquid sample zone; a reagent zone downstream and in fluid communication with the sample zone comprising a reagent cell having a line of symmetry in the direction of fluid flow; a reagent material in the reagent cell, wherein the reagent material includes a first reagent material located at the axis of symmetry and is left-right symmetric, and a second and third reagent material having a substantially identical shape and volume and located in mirror locations from the line of symmetry; a detection zone in fluid communication with the reagent zone; and a wicking zone in fluid communication with the detection zone having a capacity to receive liquid sample flowing from the detection zone, wherein the sample addition zone, the detection zone and the wicking zone define a fluid flow path.

2. An assay device as disclosed in embodiment 1, wherein first reagent material has a shape and volume such that it is the last reagent material to be completely dissolved by the fluid flow.

3. An assay device as disclosed in embodiment 2, wherein first reagent material has a larger shape or volume such that it is the last reagent material to be completely dissolved by the fluid flow.

4. An assay device as disclosed in embodiment 1, wherein first reagent material is located upstream from the second and third reagent material.

5. An assay device as disclosed in embodiment 1, wherein first reagent material is located downstream from the second and third reagent material.

6. An assay device as disclosed in embodiment 1, wherein the reagent zone has a single reagent cell.

7. An assay device as disclosed in embodiment 1, wherein the reagent zone has at least two reagent cells arranged symmetrically in the reagent zone.

8. An assay device as disclosed in embodiment 1, wherein the detection zone has a substrate and projections which extend substantially vertically from the substrate, wherein the projections have a height, cross-section and a distance between one another that defines a capillary space between the projections capable of generating capillary flow parallel to the substrate surface.

9. An assay device as disclosed in embodiment 1, wherein the reagent material comprises a labeled reagent material, and the detection zone has capture elements bound thereto.

10. An assay device as disclosed in embodiment 1, wherein the width of the flow path through the detection zones is in the range of about 0.5 to 1.2 mm.

11. An assay device as disclosed in embodiment 1, wherein first, second and third reagent materials have the same composition.

12. An assay device as disclosed in embodiment 1, wherein at least one of the first, second and third reagent materials has a different composition.

13. An assay device as disclosed in embodiment 12, wherein the first, reagent material has a first composition and the second and third reagent materials have a different, second composition.

14. A method of increasing the width of a reagent plume flowing from a reagent zone and into a detection zone in an assay device comprising: providing a liquid sample zone; providing a reagent zone downstream and in fluid communication with the sample zone comprising a reagent cell having a line of symmetry in the direction of fluid flow; providing a reagent material in the reagent cell, wherein the reagent material includes a first reagent material located at the axis of symmetry and is left-right symmetric, and a second and third reagent material having a substantially identical shape and volume and located in mirror locations from the line of symmetry; providing a detection zone in fluid communication with the reagent zone; providing a wicking zone in fluid communication with the capture zone having a capacity to receive liquid sample flowing from the capture zone, wherein the sample zone, the detection zone and the wicking zone define a fluid flow path; adding sample to the sample zone; flowing the sample from the sample zone and into the reagent zone and past the first, second and third reagent materials, whereby sample flowing past the second and third reagent materials forms a second and third reagent plumes along the edges of the reagent cell, and sample flowing past the first reagent material forms a first reagent plume along the line of symmetry of the reagent cell, and flowing the sample past the first, second and third reagent materials, whereby the first, second and third reagent plume combine to form a combined reagent plume.

15. A method as disclosed in embodiment 14, wherein the increased width of the reaction plume is relative to a reaction plume formed by a reagent cell having only a single reagent material arranged in the reagent cell.

16. A method as disclosed in embodiment 14, wherein the detection zone has a substrate and projections which extend substantially vertically from the substrate, wherein the projections have a height, cross-section and a distance between one another that defines a capillary space between the projections capable of generating capillary flow parallel to the substrate surface.

17. A method as disclosed in embodiment 14, wherein the wider reagent plume extends across the entire width of the detection zone.

18. An assay device as disclosed in embodiment 14, wherein first reagent material has a shape and volume such that it is the last reagent material to be completely dissolved by the fluid flow.

19. An assay device as disclosed in embodiment 18, wherein first reagent material has a larger shape or volume such that it is the last reagent material to be completely dissolved by the fluid flow.

20. An assay device as disclosed in embodiment 15, wherein first reagent material is located upstream from the second and third reagent material.

21. An assay device as disclosed in embodiment 14, wherein first reagent material is located downstream from the second and third reagent material.

22. An assay device as disclosed in embodiment 14, wherein first, second and third reagent materials have the same composition.

23. An assay device as disclosed in embodiment 14, wherein at least one of the first, second and third reagent materials has a different composition.

24. An assay device as disclosed in embodiment 23, wherein the first, reagent material has a first composition and the second and third reagent materials have a different, second composition.

25. A method of performing an assay on a liquid sample for the presence or concentration of one or more analyte(s) or control(s), on the assay device according to embodiment 1, comprising: depositing a liquid sample containing the analyte(s) of interest onto a sample addition zone of the assay device; moving the sample by capillary action through a fluid flow path into a reagent zone where it dissolves one or more reagents; flowing the sample away from the reagent zone having a dissolved reagent plume containing one or more reagents and into detection zone(s) by capillary action through the fluid flow path, wherein signal(s) representative of the presence or concentration of analyte(s) or control(s) is produced; and reading the signal(s) that are produced in the detection zones to determine the presence or concentration of the analytes or controls.

Those skilled in the art will appreciate that the invention and embodiments thereof described herein are susceptible to variations and modifications other than those specifically described. It is to be understood that the invention includes all such variations and modifications. The invention also includes all of the steps and features referred to in this specification, individually or collectively, and any and all combinations of any two or more of the steps or features.

What is claimed is:

1. An assay device comprising:
a liquid sample zone;
a reagent zone downstream and in fluid communication with the sample zone comprising a reagent cell having a line of symmetry in the direction of fluid flow;
a reagent material in the reagent cell, wherein the reagent material includes a first reagent material located at the axis of symmetry and is left-right symmetric, and a second and third reagent material having a substantially identical shape and volume and located in mirror locations from the line of symmetry;
a detection zone in fluid communication with the reagent zone; and
a wicking zone in fluid communication with the detection zone having a capacity to receive liquid sample flowing from the detection zone, wherein the liquid sample zone, the detection zone and the wicking zone define a fluid flow path.

2. An assay device as claimed in claim 1, wherein the first reagent material has a shape and volume such that it is the last reagent material to be completely dissolved by the fluid flow.

3. An assay device as claimed in claim 2, wherein the first reagent material has a larger shape and volume than the second and third reagent materials such that it is the last reagent material to be completely dissolved by the fluid flow.

4. An assay device as claimed in claim 1, wherein the first reagent material is located upstream from the second and third reagent material.

5. An assay device as claimed in claim 1, wherein the first reagent material is located downstream from the second and third reagent material.

6. An assay device as claimed in claim 1, wherein the reagent zone has a single reagent cell.

7. An assay device as claimed in claim 1, wherein the reagent zone has at least two reagent cells arranged symmetrically in the reagent zone.

8. An assay device as claimed in claim 1, wherein the detection zone has a substrate and projections which extend substantially vertically from the substrate, wherein the projections have a height, cross-section and a distance between one another that defines a capillary space between the projections capable of generating capillary flow parallel to the substrate surface.

9. An assay device as claimed in claim 1, wherein the reagent material comprises a labeled reagent material, and the detection zone has capture elements bound thereto.

10. An assay device as claimed in claim 1, wherein the width of the fluid flow path through the detection zones is in the range of about 0.5 to 1.2 mm.

11. An assay device as claimed in claim 1, wherein at least one of the first, second and third reagent materials has the same composition.

12. An assay device as claimed in claim 1, wherein at least one of the first, second and third reagent materials has a different composition.

13. An assay device as claimed in claim 12, wherein the first reagent material has a first composition and the second and third reagent materials have a different, second composition.

14. A method of performing an assay on a liquid sample for the presence or concentration of one or more analyte(s) of the liquid sample or control(s) on the assay device according to claim 1, comprising:
depositing a liquid sample containing the analyte(s) of interest onto a sample addition zone of the assay device;
moving the sample by capillary action through a fluid flow path into a reagent zone of the assay device where the sample dissolves one or more reagents;
flowing the sample away from the reagent zone having a dissolved reagent plume containing one or more reagents and into detection zone(s) of the assay device by capillary action through the fluid flow path, wherein signal(s) representative of the presence or concentration of analyte(s) of the sample or control(s) of the assay device is produced; and
reading the signal(s) that are produced in the detection zone(s) to determine the presence or concentration of the analyte(s) of the sample or control(s) of the assay device.

* * * * *